United States Patent
Samain et al.

(10) Patent No.: US 9,173,821 B2
(45) Date of Patent: *Nov. 3, 2015

(54) OXIDATION DYEING PROCESS USING A COMPOSITION RICH IN FATTY SUBSTANCES AND METAL CATALYSTS, AND DEVICE SUITABLE THEREFOR

(71) Applicant: L'Oreal, Paris (FR)

(72) Inventors: Henri Samain, Bièvres (FR); Leïla Hercouet, Neuilly Plaisance (FR); Marie Giafferi, Villemomble (FR); Alain Lagrange, Coupvray (FR); Marie Mignon, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/367,083

(22) PCT Filed: Dec. 20, 2012

(86) PCT No.: PCT/EP2012/076443
§ 371 (c)(1),
(2) Date: Sep. 16, 2014

(87) PCT Pub. No.: WO2013/092890
PCT Pub. Date: Jun. 27, 2013

(65) Prior Publication Data
US 2014/0353200 A1    Dec. 4, 2014

Related U.S. Application Data

(60) Provisional application No. 61/593,488, filed on Feb. 1, 2012.

(30) Foreign Application Priority Data

Dec. 20, 2011    (FR) ........................... 11 62019

(51) Int. Cl.
| *A61Q 5/10* | (2006.01) |
|---|---|
| *A61K 8/19* | (2006.01) |
| *A61K 8/31* | (2006.01) |
| *A61K 8/34* | (2006.01) |
| *A61K 8/365* | (2006.01) |
| *A61K 8/37* | (2006.01) |
| *A61K 8/20* | (2006.01) |
| *A61K 8/22* | (2006.01) |
| *A61K 8/36* | (2006.01) |
| *A61K 8/41* | (2006.01) |
| *B65D 81/32* | (2006.01) |

(52) U.S. Cl.
CPC ... *A61K 8/19* (2013.01); *A61K 8/20* (2013.01); *A61K 8/22* (2013.01); *A61K 8/31* (2013.01); *A61K 8/34* (2013.01); *A61K 8/342* (2013.01); *A61K 8/36* (2013.01); *A61K 8/365* (2013.01); *A61K 8/37* (2013.01); *A61K 8/375* (2013.01); *A61K 8/41* (2013.01); *A61K 8/415* (2013.01); *A61Q 5/10* (2013.01); *B65D 81/32* (2013.01); *A61K 2800/884* (2013.01)

(58) Field of Classification Search
CPC ............. A61Q 5/08; A61Q 5/10; A61K 8/19; A61K 8/22; A61K 2800/882; A61K 2800/884; A61K 2800/4322
USPC ............................................. 8/405
See application file for complete search history.

(56) References Cited

U.S. PATENT DOCUMENTS

| 4,620,850 A * | 11/1986 | Bachmann et al. ............... 8/406 |
| 5,112,360 A | 5/1992 | Garoche |
| 2010/0247465 A1 * | 9/2010 | Simonet et al. ................. 424/62 |
| 2010/0278767 A1 * | 11/2010 | Hoffkes et al. ................. 424/62 |

FOREIGN PATENT DOCUMENTS

| EP | 0 348 280 A1 | 12/1989 |
| EP | 0 621 029 A1 | 10/1994 |
| EP | 0 749 748 A1 | 12/1996 |
| EP | 2 332 516 A1 | 6/2011 |
| FR | 2 735 976 A1 | 1/1997 |
| FR | 2 940 079 A1 | 6/2010 |
| WO | WO 03/047542 A1 * | 6/2003 |
| WO | WO 2011/000892 A2 * | 1/2011 |

OTHER PUBLICATIONS

International Search Report mailed Dec. 4, 2013, issued in corresponding International Application No. PCT/EP2012/076443, filed Dec. 20, 2012, 3 pages.

* cited by examiner

Primary Examiner — Eisa Elhilo
(74) Attorney, Agent, or Firm — Christensen O'Connor Johnson Kindness PLLC

(57) ABSTRACT

The present invention relates to a process for dyeing keratin fibers, in particular human keratin fibers such as the hair, comprising the use of one or more metal catalysts chosen from transition metal salts and rare-earth metal salts, and mixtures thereof and a composition (I) comprising at least 10% by weight of one or more fatty substances different from fatty acids, one or more oxidation dyes and one or more oxidizing agents.

18 Claims, No Drawings

OXIDATION DYEING PROCESS USING A COMPOSITION RICH IN FATTY SUBSTANCES AND METAL CATALYSTS, AND DEVICE SUITABLE THEREFOR

The present invention relates to a process for dyeing keratin fibres, in particular human keratin fibres such as the hair, comprising the use of one or more metal catalysts chosen from transition metal salts and rare-earth metal salts, and mixtures thereof and a composition comprising at least 10% by weight of one or more fatty substances different from fatty acids, one or more oxidation dyes and one or more oxidizing agents.

The present invention relates to the field of the dyeing of keratinous fibres and more particularly to the field of hair dyeing.

Many people have sought for a long time to modify the colour of their hair and in particular to mask their grey hair.

It is known practice to obtain "permanent" coloration or oxidation dyeing with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds, such as indole compounds. The variety of the molecules used as oxidation bases and couplers allows a wide range of colours to be obtained.

The permanent dyeing process thus consists in applying to the keratin fibres bases or a mixture of bases and couplers with hydrogen peroxide ($H_2O_2$ or aqueous hydrogen peroxide solution), as oxidizing agent, in leaving it to diffuse, and then in rinsing the fibres. The colorations which result therefrom have the advantage of being permanent, strong and resistant to external agents, in particular to light, bad weather, washing, perspiration and rubbing.

However, it is sought to further increase the reaction efficacy of the oxidation dyes used during this process in order to improve their buildup on the keratin fibres. Specifically, such an improvement would especially make it possible to reduce the amounts of oxidation dyes present in dye compositions, to reduce the leave-on time on keratin fibres and/or to use other families of dyes that have poor dyeing power but that are capable of presenting a good toxicological profile, of providing novel shades or of leading to colorations that are fast with respect to external agents such as light or shampoo.

In this regard, it has already been proposed to use cosmetic compositions containing metal catalysts in a dyeing process in order to accelerate the oxidation reaction of the dyes and to improve the intensity of the coloration on keratin fibres. However, the dyeing power obtained is still not entirely satisfactory and the colorations obtained are generally too selective, i.e. these colorations are not homogeneous along the keratin fibre.

There is thus a real need to propose dyeing processes performed in the presence of an oxidizing agent, which do not have the drawbacks of the existing processes, i.e. which are capable of leading to satisfactory intensity of the oxidation dyes on keratin fibres, while at the same time producing sparingly selective colorations.

This aim is achieved by the present invention, one subject of which is especially a process for dyeing keratin fibres, in particular human keratin fibres such as the hair, comprising the use of one or more metal catalysts chosen from transition metal salts and rare-earth metal salts, and mixtures thereof, and of a composition (I) comprising:

(a) at least 10% of one or more fatty substances different from fatty acids relative to the total weight of composition (I), (b) one or more oxidation dyes, and (c) one or more oxidizing agents.

The dyeing process according to the invention produces a satisfactory colour intensity on keratin fibres while at the same time being sparingly selective, i.e. giving homogeneous colorations along the keratin fibre.

In particular, the use of the dyeing process according to the invention prevents the metal catalysts from halting the action of the oxidation dyes on keratin fibres, in contrast with conventional dyeing processes involving the use of metal catalysts.

Moreover, the dyeing process according to the invention improves the intensity of the coloration on keratin fibres when compared with a dyeing process not involving the use of one or more metal catalysts.

Furthermore, the process according to the present invention leads to strong, chromatic colorations.

In the process of the invention, the metal catalyst(s) may constitute or form part of a composition (A) which may be mixed with composition (I) before applying the mixture to keratin fibres or applied separately as a pre-treatment or post-treatment with or without intermediate rinsing. It should be noted that the composition may consist solely of the metal catalyst(s).

The present invention also relates to a multi-compartment device comprising a first compartment containing a cosmetic composition (A) comprising one or more metal catalysts chosen from transition metal salts and rare-earth metal salts, and mixtures thereof, a second compartment containing a cosmetic composition (B) comprising one or more oxidation dyes, and a third compartment containing a composition (C) comprising one or more oxidizing agents, at least one fatty substance different from fatty acids, the fatty substance being present in at least one of the compositions (B) or (C) such that, after mixing together compositions (B) and (C), the fatty substance content is greater than or equal to 10% by weight relative to the total weight of the mixture of compositions (B) and (C).

According to one particular embodiment, the device comprises a fourth compartment comprising a composition (D) comprising one or more fatty substances as previously defined, the said composition (D) being intended to be mixed with compositions (B) and (C), the fatty substance content being greater than or equal to 10% by weight relative to the total weight of the mixture of compositions (B), (C) and (D), composition (B) or (C) optionally containing one or more fatty substances.

Other characteristics and advantages of the invention will emerge more clearly on reading the description and the examples that follow.

In the text hereinbelow, and unless otherwise indicated, the limits of a range of values are included within that range.

The expression "at least one" is equivalent to the expression "one or more".

The human keratin fibres treated via the process according to the invention are preferably the hair.

The dyeing process according to the present invention uses one or more metal catalysts.

Metal catalysts are compounds comprising one or more metals in their structure.

The metals are chosen from transition metals, rare-earth metals and alloys thereof.

In particular, the metals are chosen from transition metals and rare-earth metals.

Among the transition metals, mention may be made especially of manganese, iron, cobalt, copper, zinc, platinum, nickel, titanium, silver, zirconium, chromium, molybdenum, tungsten, platinum, gold and vanadium, and among these most particularly manganese.

Among the rare-earth metals, mention may be made especially of cerium.

Thus, the metal catalysts are especially catalysts based on transition metals and rare-earth metals, and more particularly catalysts based on manganese, vanadium or cerium.

The metal catalysts are metal salts which are chosen from transition metal salts and rare-earth metal salts and also mixtures thereof.

For the purposes of the present invention, the term "metal salts" means salts derived from the action of an acid on a metal.

Preferentially, the metal catalysts used in the dyeing process are chosen from transition metal salts, such as manganese salts, and rare-earth metal salts, such as cerium salts, and also mixtures thereof.

The metal salts may be inorganic or organic salts.

The inorganic metal salts may be chosen from halides, carbonates, sulfates and phosphates, especially hydrated or anhydrous halides.

The organic metal salts may be chosen from organic acid salts such as citrates, lactates, glycolates, gluconates, acetates, propionates, fumarates, oxalates and tartrates, especially gluconates.

Preferentially, the metal catalysts are chosen from organic acid salts of transition metals, especially of manganese, and inorganic salts of rare-earth metals, especially of cerium.

More preferentially, the metal catalysts are chosen from manganese gluconate and cerium chloride heptahydrate, especially manganese gluconate.

The metal catalysts may be present in a content ranging from 0.001% to 10% by weight, preferably in a content ranging from 0.001% to 1% by weight and better still ranging from 0.01% to 0.5% by weight relative to the total weight of the composition applied to the keratin fibres containing them.

The metal catalyst(s) may constitute all or part of a composition A.

This composition A may be anhydrous or aqueous.

When composition A is aqueous, the metal catalyst(s) may be present in a content ranging from 0.001% to 10% by weight, preferably in a content ranging from 0.001% to 1% by weight and better still ranging from 0.01% to 0.5% by weight relative to the total weight of the composition applied to the keratin fibres containing them.

As indicated previously, the dyeing process uses the cosmetic composition (I).

As has been mentioned, the cosmetic composition (I) comprises one or more fatty substances different from fatty acids.

The term "fatty substance" means an organic compound that is insoluble in water at ordinary room temperature (25° C.) and at atmospheric pressure (760 mmHg) (solubility of less than 5%, preferably 1% and even more preferentially 0.1%). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

These fatty substances are neither polyoxyethylenated nor polyglycerolated. They are different from fatty acids, since salified fatty acids constitute soaps that are generally soluble in aqueous media.

The fatty substances are especially chosen from $C_6$-$C_{16}$ hydrocarbons, hydrocarbons containing more than 16 carbon atoms and in particular alkanes, oils of animal origin, oils of plant origin, glycerides or fluoro oils of synthetic origin, fatty alcohols, fatty acid and/or fatty alcohol esters, non-silicone waxes and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they are linear, branched or possibly cyclic. Mention may be made, by way of example, of hexane, dodecane or isoparaffins, such as isohexadecane or isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the animal oils, mention may be made of perhydrosqualene.

Among the triglycerides of plant or synthetic origin, mention may be made of liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, jojoba oil, shea butter oil and caprylic/capric acid triglycerides, for instance those sold by the company Stéarineries Dubois or those sold under the names Miglyol® 810, 812 and 818 by the company Dynamit Nobel.

Among the fluoro oils, mention may be made of perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-(trifluoromethyl)perfluoromorpholine sold under the name PF 5052® by the company 3M.

The fatty alcohols that may be used in the cosmetic composition (I) are saturated or unsaturated, and linear or branched, and comprise from 6 to 30 carbon atoms and more particularly from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The wax(es) that may be used in the anhydrous cosmetic composition (I) are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the esters of a fatty acid and/or of a fatty alcohol, which are advantageously different from the triglycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates; 2-ethylhexyl palmitate; 2-octyldecyl palmitate; alkyl myristates, such as isopropyl, butyl, cetyl, 2-octyldodecyl, myristyl or stearyl myristate; hexyl stearate; butyl stearate; isobutyl stearate; dioctyl malate; hexyl laurate or 2-hexyldecyl laurate.

Still within the context of this alternative form, use may also be made of esters of $C_4$-$C_{22}$ di- or tricarboxylic acids and of $C_1$-$C_{22}$ alcohols and esters of mono-, di- or tricarboxylic acids and of di-, tri-, tetra- or pentahydroxy $C_2$-$C_{26}$ alcohols.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl traisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition can also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched $C_6$-$C_{30}$ and preferably $C_{12}$-$C_{22}$ fatty acids. If they are unsaturated, these compounds can comprise from one to three conjugated or non-conjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose.

Mention may be made, by way of example, of the product sold under the name Glucate® DO by Amerchol, which is a methylglucose dioleate.

Mention may also be made, by way of examples of esters or mixtures of esters of sugar and of fatty acid, of:
  the products sold under the names F160, F140, F110, F90, F70 and SL40 by Crodesta, respectively denoting sucrose palmitate/stearates formed of 73% monoester and 27% di- and triester, of 61% monoester and 39% di-, tri- and tetraester, of 52% monoester and 48% di-, tri- and tetraester, of 45% monoester and 55% di-, tri- and tetraester, and of 39% monoester and 61% di-, tri- and tetraester, and sucrose monolaurate;
  the products sold under the name Ryoto Sugar Esters, for example referenced B370 and corresponding to sucrose behenate formed of 20% monoester and 80% diester, triester and polyester;
  the sucrose monopalmitate/stearate-dipalmitate/stearate sold by Goldschmidt under the name Tegosoft® PSE.

The silicones that can be used in the cosmetic composition (I) of the present invention are volatile or non-volatile, cyclic, linear or branched silicones, which are unmodified or modified with organic groups, having a viscosity from $5 \times 10^{-6}$ to 2.5 m²/s at 25° C., and preferably $1 \times 10^{-5}$ to 1 m²/s.

The silicones which can be used in accordance with the invention can be provided in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in more detail in Walter Noll's "Chemistry and Technology of Silicones" (1968), Academic Press. They can be volatile or non-volatile.

When they are volatile, the silicones are more particularly chosen from those having a boiling point of between 60° C. and 260° C., and more particularly still from:
  (i) cyclic polydialkylsiloxanes comprising from 3 to 7 and preferably from 4 to 5 silicon atoms. They are, for example, octamethylcyclotetrasiloxane, sold in particular under the name Volatile Silicone® 7207 by Union Carbide or Silbione® 70045 V2 by Rhodia, decamethylcyclopentasiloxane, sold under the name Volatile Silicone® 7158 by Union Carbide and Silbione® 70045 V5 by Rhodia, and mixtures thereof.

Mention may also be made of cyclocopolymers of the dimethylsiloxane/methylalkylsiloxane type, such as Volatile Silicone® FZ 3109, sold by Union Carbide, having the formula:

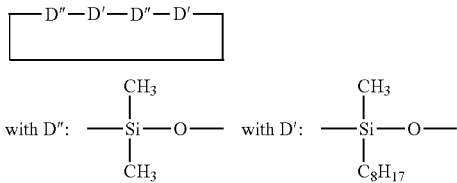

Mention may also be made of mixtures of cyclic polydialkylsiloxanes with organic compounds derived from silicon, such as the mixture of octamethylcyclotetrasiloxane and tetra (trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones coming within this category are also described in the paper published in Cosmetics and Toiletries, Vol. 91, January 76, pp. 27-32, Todd & Byers, Volatile Silicone Fluids for Cosmetics.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without implied limitation, of the following commercial products:
  the Silbione® oils of the 47 and 70 047 series or the Mirasil® oils sold by Rhodia, such as, for example, the oil 70 047 V 500 000;
  the oils of the Mirasil® series sold by Rhodia;
  the oils of the 200 series from Dow Corning, such as DC200 having a viscosity of 60 000 mm$^2$/s;
  the Viscasil® oils from General Electric and certain oils of the SF series (SF 96, SF 18) from General Electric.

Mention may also be made of polydimethylsiloxanes having dimethylsilanol end groups known under the name of dimethiconol (CTFA), such as the oils of the 48 series from Rhodia.

Mention may also be made, in this category of polydialkylsiloxanes, of the products sold under the names Abil Wax® 9800 and 9801 by Goldschmidt, which are polydi(C$_1$-C$_{20}$) alkylsiloxanes.

The silicone gums which can be used in accordance with the invention are in particular polydialkylsiloxanes and preferably polydimethylsiloxanes having high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products which can be used more particularly in accordance with the invention are mixtures, such as:
  the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;
  the mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;
  the mixtures of two PDMSs with different viscosities, and more particularly of a PDMS gum and a PDMS oil, such as the product SF 1236 from General Electric. The product SF 1236 is the mixture of a gum SE 30 defined above having a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins which can be used in accordance with the invention are crosslinked siloxane systems including the following units:

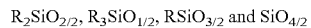

in which R represents an alkyl having from 1 to 16 carbon atoms. Among these products, those that are particularly preferred are those in which R denotes a lower C$_1$-C$_4$ alkyl group, more particularly methyl.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold in particular under the names X22-4914, X21-5034 and X21-5037 by Shin-Etsu.

The organomodified silicones which can be used in accordance with the invention are silicones as defined above comprising, in their structure, one or more organofunctional groups attached via a hydrocarbon group.

In addition to the silicones described above, the organomodified silicones can be polydiarylsiloxanes, in particular polydiphenylsiloxanes, and polyalkylarylsiloxanes functionalized by the abovementioned organo functional groups.

The polyalkylarylsiloxanes are chosen in particular from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:
  Silbione® oils of the 70 641 series from Rhodia;
  the oils of the Rhodorsil® 70 633 and 763 series from Rhodia;
  the oil Dow Corning 556 Cosmetic Grade Fluid from Dow Corning;
  the silicones of the PK series from Bayer, such as the product PK20;
  the silicones of the PN and PH series from Bayer, such as the products PN1000 and PH1000;
  certain oils of the SF series from General Electric, such as SF 1023, SF 1154, SF 1250 and SF 1265.

Mention may be made, among the organomodified silicones, of polyorganosiloxanes comprising:

polyethyleneoxy and/or polypropyleneoxy groups optionally comprising $C_6$-$C_{24}$ alkyl groups, such as the products named dimethicone copolyol sold by Dow Corning under the name DC 1248 or the oils Silwet® L 722, L 7500, L 77 and L 711 by Union Carbide, and the ($C_{12}$) alkyl methicone copolyol sold by Dow Corning under the name Q2 5200;

substituted or unsubstituted amino groups, such as the products sold under the names GP 4 Silicone Fluid and GP 7100 by Genesee or the products sold under the names Q2 8220 and Dow Corning 929 or 939 by Dow Corning. The substituted amino groups are in particular $C_1$-$C_4$ aminoalkyl groups;

alkoxylated groups, such as the product sold under the name Silicone Copolymer F-755 by SWS Silicones, and Abil Wax® 2428, 2434 and 2440 by Goldschmidt.

Preferably, the fatty substances do not comprise any $C_2$-$C_3$ oxyalkylene units or any glycerol units. Preferably, the fatty substances are not salified fatty acids or soaps, which are water-soluble compounds.

The fatty substances are advantageously chosen from $C_6$-$C_{16}$ hydrocarbons, hydrocarbons containing more than 16 carbon atoms and in particular alkanes, oils of plant origin, fatty alcohols, fatty acid and/or fatty alcohol esters, and silicones, or mixtures thereof.

Preferably, the fatty substance is an oil (a compound that is liquid at a temperature of 25° C. and at atmospheric pressure).

Preferably, the fatty substance is chosen from liquid petrolatum, $C_6$-$C_{16}$ alkanes, polydecenes, liquid fatty acid and/or fatty alcohol esters, liquid fatty alcohols or their mixtures. Better still, the fatty substance is chosen from liquid petrolatum, $C_6$-$C_{16}$ alkanes or polydecenes.

The fatty substances are present in a content of greater than or equal to 10% by weight relative to the total weight of the cosmetic composition (I).

Composition (I) has a fatty substance content preferably ranging from 10% to 70% by weight, even more particularly ranging from 20% to 70% by weight, better still from 25% to 70% by weight, even better still from 25% to 60% by weight and most particularly from 30% to 60% by weight relative to the total weight of composition (I).

Composition (I) and/or composition (A) may also comprise one or more surfactants.

More particularly, the surfactant(s) are chosen from nonionic surfactants and anionic surfactants.

The term "anionic surfactant" means a surfactant comprising, as ionic or ionizable groups, only anionic groups. These anionic groups are preferably chosen from $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2$, $HPO_2^-$, $PO_2^-$, $POH$ and $PO^-$ groups.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, alpha-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl lactylates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_{6-24}$ alkyl monoesters and polyglycoside-polycarboxylic acids may be selected from $C_{6-24}$ alkyl polyglycoside-citrates, $C_{6-24}$ alkyl polyglycoside-tartrates and $C_{6-24}$ alkyl polyglycoside-sulfo succinates.

When the anionic surfactant(s) are in salt form, they may be chosen from alkali metal salts, such as the sodium or potassium salt and preferably the sodium salt, ammonium salts, amine salts and in particular amino alcohol salts, or alkaline-earth metal salts, such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Among the anionic surfactants, it is preferred, according to the invention, to use alkyl sulfate salts and alkyl ether sulfate salts, and alkyl ether carboxylic acids and salts thereof, and mixtures thereof.

The anionic surfactants are more especially chosen from the salts (in particular alkali metal salts, especially sodium salts, ammonium salts or alkaline-earth metal salts such as magnesium salts) of the following compounds:

alkyl sulfates, alkyl ether sulfates, alkylamido ether sulfates, alkylaryl polyether sulfates, monoglyceride sulfates;

alkylsulfonates, alkylamidesulfonates, alkylarylsulfonates, α-olefinsulfonates, paraffinsulfonates;

alkyl phosphates, alkyl ether phosphates;

alkylsulfosuccinates, alkyl ether sulfosuccinates, alkylamidesulfosuccinates; alkylsulfosuccinates;

alkylsulfoacetates;

acylsarcosinates; acylisethionates and N-acyltaurates;

salts of fatty acids such as oleic acid, ricinoleic acid, palmitic acid or stearic acid, coconut oil acid or hydrogenated coconut oil acid;

alkyl-D-galactoside uronic acid salts;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, in particular those containing from 2 to 50 ethylene oxide groups;

and mixtures thereof.

It should be noted that the alkyl or acyl radical of these various compounds advantageously contains from 6 to 24 carbon atoms and preferably from 8 to 24 carbon atoms, and the aryl radical preferably denotes a phenyl or benzyl group.

The nonionic surfactants are chosen more particularly from mono- or polyoxyalkylenated or mono- or polyglycerolated nonionic surfactants. The oxyalkylene units are more particularly oxyethylene or oxypropylene units, or their combination, preferably oxyethylene units.

Examples of nonionic surfactants that can be used in the composition used according to the invention are described, for example, in the Handbook of Surfactants by M. R. Porter, published by Blackie & Son (Glasgow and London), 1991, pp. 116-178. They are especially chosen from alcohols, α-diols and ($C_1$-$C_{20}$)alkylphenols, these compounds being polyethoxylated, polypropoxylated and/or polyglycerolated, and containing at least one fatty chain comprising, for example, from 8 to 40 carbon atoms, it being possible for the number of ethylene oxide and/or propylene oxide groups to especially range from 2 to 200, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkyl glucamine and of N-acyl methylglucamine, aldobionamides, oxyethylenated and/or oxypropylenated silicones and amine oxides.

Mention may be made, as examples of oxyalkylenated nonionic surfactants, of:
oxyalkylenated ($C_8$-$C_{24}$)alkylphenols,
saturated or unsaturated, linear or branched, oxyalkylenated $C_8$-$C_{30}$ alcohols,
saturated or unsaturated, linear or branched, oxyalkylenated $C_8$-$C_{30}$ amides,
esters of saturated or unsaturated, linear or branched, $C_8$-$C_{30}$ acids and of polyethylene glycols,
polyoxyethylenated esters of saturated or unsaturated, linear or branched, $C_8$-$C_{30}$ acids and of sorbitol,
oxyethylenated and saturated or unsaturated vegetable oils,
condensates of ethylene oxide and/or of propylene oxide, inter alia,
or mixtures thereof.

Preferably, the surfactants contain a number of moles of ethylene oxide and/or of propylene oxide of between 1 and 100 and preferably between 2 and 50. Advantageously, the nonionic surfactants do not comprise oxypropylene units.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

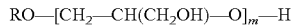

RO—[$CH_2$—$CH(CH_2OH)$—O]$_m$—H in which R represents a linear or branched $C_8$-$C_{40}$ and preferably $C_8$-$C_{30}$ alkyl or alkenyl radical and m represents a number ranging from 1 to 30 and preferably from 1 to 10.

Mention may be made, as examples of compounds which are suitable in the context of the invention, of lauryl alcohol comprising 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The alcohol can represent a mixture of alcohols in the same way that the value of m represents a statistical value, which means that, in a commercial product, several types of polyglycerolated fatty alcohols can coexist in the form of a mixture.

Use is more preferably made, among the mono- or polyglycerolated alcohols, of the $C_8/C_{10}$ alcohol comprising 1 mol of glycerol, the $C_{10}/C_{12}$ alcohol comprising 1 mol of glycerol and the $C_{12}$ alcohol comprising 1.5 mol of glycerol.

In accordance with a preferred embodiment of the invention, the oxyalkylenated nonionic surfactants are chosen from oxyethylenated $C_8$-$C_{30}$ alcohols and polyoxyethylenated esters of saturated or unsaturated and linear or branched $C_8$-$C_{30}$ acids and of sorbitol.

Preferably, the cosmetic composition (I) comprises one or more nonionic surfactants.

The surfactant content of the compositions (A) and/or (I) more particularly represents from 0.1% to 50% by weight and preferably from 0.5% to 30% by weight relative to the weight of the composition under consideration.

Compositions (A) and/or (I) may also contain various adjuvants conventionally used in hair dye compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners other than the polymers mentioned previously; antioxidants; penetrants; sequestrants; fragrances; dispersants; film-forming agents; ceramides; preserving agents; opacifiers.

The above adjuvants are generally present in an amount, for each of them, of between 0.01% and 20% by weight relative to the weight of the composition under consideration.

According to one advantageous variant of the invention, the anhydrous composition (I) comprises one or more mineral thickeners chosen from organophilic clays.

The organophilic clay can be chosen from montmorillonite, bentonite, hectorite, attapulgite, sepiolite and mixtures thereof. The clay is preferably a bentonite or a hectorite.

These clays can be modified with a chemical compound chosen from quaternary ammoniums, tertiary amines, amine acetates, imidazolines, amine soaps, fatty sulfates, alkylarylsulfonates and amine oxides, and mixtures thereof.

Organophilic clays that may be mentioned include quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; quaternium-18/benzalkonium bentonites, such as those sold under the names Claytone HT and Claytone PS by Southern Clay; quaternium-18 hectorites, such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by Rheox, and Simagel M and Simagel SI 345 by Biophil.

Preferably, the composition comprises an organomodified bentonite or hectorite.

When it is present, the inorganic thickening agent represents from 1% to 30% by weight relative to the weight of the composition.

Advantageously, the composition is in the form of a gel or a cream.

The process according to the present invention is performed in the presence of a cosmetic composition (I) comprising one or more oxidation dyes.

The oxidation dyes are generally chosen from oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloro aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Preference is particularly given, among the abovementioned para-phenylenediamines, to para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylamino ethyloxy-para-phenylenediamine and the addition salts thereof with an acid.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and the addition salts thereof with an acid.

Among the ortho-aminophenols that may be mentioned, for example, are 2-aminophenol, 2-amino-5-methylphenol, 2-amino-6-methylphenol, 5-acetamido-2-aminophenol and the addition salts thereof.

Among the heterocyclic bases that may be mentioned, for example, are pyride derivatives, pyrimidine derivatives and pyrazole derivatives.

Among the pyride derivatives that may be mentioned are the compounds described, for example, in patents GB 1 026 978 and GB 1 153 196, for instance 2,5-diaminopyride, 2-(4-methoxyphenyl)amino-3-aminopyride and 3,4-diaminopyride, and the addition salts thereof.

Other pyride oxidation bases that are useful in the present invention are the 3-aminopyrazolo[1,5-a]pyride oxidation bases or their addition salts described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyride-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyride, 3,4-diaminopyrazolo[1,5-a]pyride, pyrazolo[1,5-a]pyride-3,7-diamine, 7-(morpholin-4-yl)pyrazolo[1,5-a]pyrid-3-ylamine, pyrazolo[1,5-a]pyride-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyrid-5-ol, 3-aminopyrazolo[1,5-a]pyrid-4-ol, 3-aminopyrazolo[1,5-a]pyrid-6-ol, 3-aminopyrazolo[1,5-a]pyrid-7-ol and the addition salts thereof.

Among the pyrimidine derivatives that may be mentioned are the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used.

Use will preferably be made of a 4,5-diaminopyrazole and even more preferentially of 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2- dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or a salt thereof.

The cosmetic composition (I) according to the invention may optionally comprise one or more couplers advantageously chosen from those conventionally used for the dyeing of keratin fibres.

Among these couplers, mention may be made especially of meta-phenylenediamines, meta-aminophenols, meta-diphenols, monophenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyride, 6-hydroxybenzomorpholine, 3,5-diamino-2,6-dimethoxypyride, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyride, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that can be used within the context of the invention are especially chosen from the addition salts with an acid such as the hydrochlorides, hydrobromides, sulfates, citrates, succinates, tartrates, lactates, tosylates, benzenesulfonates, phosphates and acetates.

According to one particular embodiment, composition (I) comprises at least one oxidation base, which is preferably heterocyclic, and at least one monophenolic coupler, guaiacol, arbutin, thymol, sesamol, carvacrol, syringol or vanillin.

The oxidation base(s) each advantageously represent from 0.0001% to 10% by weight relative to the total weight of the composition, and preferably from 0.005% to 5% by weight relative to the total weight of the composition.

The content of coupler(s), if they are present, each advantageously represents from 0.0001% to 10% by weight relative to the total weight of the composition, and preferably from 0.005% to 5% by weight relative to the total weight of the cosmetic composition (C).

Compositions (A) and (I) may be anhydrous or aqueous.

More particularly, for the purposes of the invention, the expression "anhydrous cosmetic composition" means a cosmetic composition with a water content of less than 5% by weight, preferably less than 2% by weight and more preferably still less than 1% by weight relative to the weight of said composition. It should be noted that the water in question is more particularly bound water, such as water of crystallization in salts, or traces of water absorbed by the raw materials used in the production of the compositions according to the invention.

The term "aqueous composition" is understood to mean a composition comprising more than 5% by weight of water, preferably more than 10% by weight of water and more advantageously still more than 20% by weight of water.

Preferably, the cosmetic composition (I) is an aqueous composition.

Even more preferentially, the water concentration of composition (I) may range from 10% to 90% and better still from 20% to 80% of the total weight of the composition.

Compositions (A) and (I) may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

The organic solvent(s), if they are present, represent a content usually ranging from 1% to 40% by weight and preferably from 5% to 30% by weight relative to the weight of the cosmetic composition (C).

The pH of compositions (A) and (I), if they are aqueous, ranges from 2 to 13. For composition (I), it preferably ranges from 6.5 to 12 and better still from 8 to 12. The pH is adapted by using additional acidifying or basifying agents, such as those mentioned below.

Among the additional acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

As regards the additional basifying agent, if it is present, it may be chosen from non-salified organic amines comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for use.

Among compounds of this type, mention may be made of monoethanolamine, diethanolamine, triethanolamine, mono isopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Also suitable are the organic amines of the following formula:

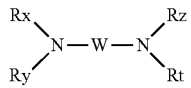

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

Preferably, the cosmetic composition (I) comprises one or more organic amines chosen from alkanolamines, especially monoethanolamine.

Finally, the process is performed with a composition (I) comprising one or more oxidizing agents.

More particularly, the oxidizing agent(s) are chosen from hydrogen peroxide, urea peroxide, alkali metal bromates or ferricyanides, peroxygenated salts, for instance alkali metal or alkaline-earth metal persulfates, perborates, peracids and precursors thereof, and percarbonates of alkali metals or alkaline-earth metals, and peracids and precursors thereof.

The oxidizing agent is preferably hydrogen peroxide.

This oxidizing agent advantageously consists of hydrogen peroxide, in particular in aqueous solution (aqueous hydrogen peroxide solution), the concentration of which may vary, more particularly from 0.1% to 50% by weight, even more preferentially from 0.5% to 20% by weight and better still from 1% to 15% by weight relative to composition (I).

As indicated previously, composition (I) may result from the mixing of a composition (B) comprising one or more oxidation dyes as defined previously and a composition (C) comprising one or more oxidizing agents as defined previously. Compositions (B) and (C) are preferably aqueous. They may especially be in the form of direct or inverse emulsions.

They may also result from the mixing of three compositions, the first two being compositions (A) and (B) above and the third composition being a composition (D) comprising at least one fatty substance as defined previously.

This composition (D) may be anhydrous or aqueous. It is preferably anhydrous.

Usually, the pH of the oxidizing composition (C), when it is aqueous, is less than 7.

In accordance with a first variant of the present invention, compositions (A) and (I) are mixed together, and the mixture made is then applied to wet or dry keratin fibres.

In a second variant of the invention, composition (A) and composition (I) resulting from the extemporaneous mixing of compositions (B), (C) and optionally (D) are applied successively to wet or dry keratin fibres, with or without intermediate rinsing.

Preferably, in this second variant, there is no intermediate rinsing.

Preferably, in this second variant, composition (A) is applied before composition (I).

The leave-on time of composition (A) on the keratin fibres may range from 5 to 15 minutes and is preferably 10 minutes.

In particular, composition (A) is applied to the keratin fibres and is left on for 10 minutes at room temperature.

Preferably, composition (A) is sprayed onto the keratin fibres.

In addition, composition (I), which is a mixture of compositions (B), (C) and optionally (D), may be left in place on the keratin fibres for a time generally from about 1 minute to 1 hour, preferably from 5 minutes to 40 minutes and preferably for 35 minutes.

The temperature during the process is conventionally between room temperature (between 15 and 25° C.) and 80° C. and preferably between room temperature and 60° C.

According to one preferred embodiment, composition (A) is applied to wet or dry keratin fibres and the fibres are then dried at a temperature ranging from room temperature to 60° C., preferably at 60° C., followed by the successive application, without intermediate rinsing, of composition (I) resulting from the extemporaneous mixing before application of compositions (B), (C) and optionally (D).

The drying step may last for 5 to 20 minutes and preferably for 5 to 15 minutes, and is especially 10 minutes.

After the treatment, the human keratin fibres are optionally rinsed with water, optionally washed with a shampoo and then rinsed with water, before being dried or left to dry.

Preferably, after the treatment, the keratin fibres are dried under a hood at a temperature ranging from 50 to 80° C.

According to one embodiment, the process for dyeing keratin fibres comprises the use:

(a) of a composition (A) comprising one or more metal catalysts chosen from transition metal salts, in particular organic acid salts of transition metals, and rare-earth metal salts, in particular inorganic salts of rare-earth metals, preferably manganese salts, (b) of an anhydrous composition (B) comprising one or more fatty substances chosen from liquid petroleum jelly, $C_6$-$C_{16}$ alkanes, polydecenes liquid esters of fatty acids and/ or of fatty alcohols, and liquid fatty alcohols, or mixtures thereof, (c) of a cosmetic composition (C) comprising one or more oxidation dyes, (d) of an oxidizing composition (D) comprising one or more oxidizing agents, and in which composition (A) is applied to the keratin fibres, followed by the successive application to the said fibres, without intermediate rinsing, of the composition resulting from the extemporaneous mixing of compositions (B), (C) and (D).

Finally, the invention relates to a multi-compartment device comprising a first compartment containing a cosmetic composition (A) comprising one or more metal catalysts as previously defined, a second compartment containing a cosmetic composition (B) comprising one or more oxidation dyes as defined previously, and a third compartment containing a composition (C) comprising one or more oxidizing agents as defined previously, at least one fatty substance as defined previously being present in at least one of the compositions (B) or (C) such that, after mixing together compositions (B) and (C), the fatty substance content is greater than or equal to 10% by weight relative to the total weight of the mixture of compositions (B) and (C). According to one particular embodiment, the device comprises a fourth compartment comprising a composition (D) comprising one or more fatty substances, the said composition (D) being intended to be mixed with compositions (B) and (C), the fatty substance content being greater than or equal to 10% by weight relative to the total weight of the mixture of compositions (B), (C) and (D), composition (B) or (C) optionally containing one or more fatty substances.

The device is suitable for implementing the dyeing process according to the invention.

The examples that follow serve to illustrate the invention without, however, being limiting in nature.

EXAMPLE 1

I. Compositions Tested

1. Preparation of the Composition Based on Metal Salts

Composition (A1) based on metal salts is prepared (the amounts are expressed as weight percentages).

| Composition | A1 |
|---|---|
| Manganese gluconate | 0.1 |
| Demineralized water | q.s. for 100 |
| pH | 6.52 |

3. Preparation of a Dye Composition I

Compositions (D), (B) and (C) below are prepared (the amounts are expressed as weight percentages):

| Anhydrous composition | D |
|---|---|
| Liquid petrolatum | 64.5 |
| 2-Octyldodecanol | 11.5 |
| Distearyldimethylammonium-modified hectorite | 3 |
| Propylene carbonate | 1 |
| Oxyethylenated sorbitan monolaurate (4 OE) | 11 |
| Glycol distearate | 8 |
| Oxyethylenated (2 OE) lauryl alcohol | 1 |

| Composition | B |
|---|---|
| 1-Methyl-2,5-diaminobenzene | 7 |
| N,N-Bis(2-hydroxyethyl)-p-phenylenediamine sulfate monohydrate | 1.55 |
| Resorcinol | 4.3 |
| 1-Hydroxy-3-aminobenzene | 2.1 |
| 6-Hydroxybenzomorpholine | 0.47 |
| 1-β-Hydroxyethyloxy-2,4-diaminobenzene dihydrochloride | 2.25 |
| Monoethanolamine | 13.66 |
| Sodium metabisulfite | 0.70 |
| L-Ascorbic acid | 0.25 |
| Diethylenetriaminepentaacetic acid pentasodium salt as a 40% aqueous solution | 1 |
| Hydroxyethyl cellulose | 1.5 |
| Propylene glycol | 6.2 |
| Ethanol | 8.25 |
| Hexylene glycol | 3.00 |
| Dipropylene glycol | 3.00 |
| Demineralized water | q.s. for 100 |

| Oxidizing composition | C |
|---|---|
| 50% hydrogen peroxide solution | 12 |
| Liquid petrolatum | 20 |
| Cetylstearyl alcohol (30/70 $C_{16}/C_{18}$) | 8 |
| Oxyethylenated cetearyl alcohol (33 EO) | 3 |
| Tetrasodium pyrophosphate decahydrate | 0.03 |
| Crystalline sodium hexahydroxystannate | 0.04 |
| Diethylenetriaminepentaacetic acid pentasodium salt as a 40% aqueous solution | 0.15 |
| Non-stabilized polydimethyldiallylammonium chloride in water at 40% by weight | 0.5 |
| Poly[(dimethyliminio)-1,3-propanediyl(dimethyliminio)-1,6-hexanediyl dichloride]as an aqueous 60% solution | 0.25 |
| Phosphoric acid | qs pH |
| Protected oxyethylenated rapeseed acid amides (4 OE) | 1.3 |
| Vitamin E | 0.1 |
| Glycerol | 0.5 |
| Demineralized water | q.s. for 100 |

At the time of use, 10 g of the anhydrous composition (D), 4 g of composition (B) and 15 g of composition (C) are mixed together to obtain a dye composition I. The pH of composition I is 9.7.

II. Procedure

Composition (A1) based on metal salts is sprayed onto natural grey hair (NG) containing 90% white hairs and permanent-waved grey hair (PWG) containing 90% white hairs, which are placed vertically on a support. The "composition/lock" bath ratio is respectively 1/1 (g/g). The leave-on time is 10 minutes at ambient temperature.

The locks of hair are then dried under a hood at a temperature of 60° C. for 10 minutes.

Dye composition 1 is then applied to each of the locks. The "composition/lock" bath ratio is respectively 1/1 (g/g). The locks of hair are again placed vertically on a support for 35 minutes at room temperature.

After this leave-on time, the locks of hair are washed with iNOA POST shampoo, rinsed and then dried under a hood at a temperature of 60° C.

III. Results

The colour of the locks was evaluated in the CIE L*a*b* system, using a Minolta Spectrophotometer CM2600D colorimeter. In this L*a*b* system, L* represents the intensity of the colour, a* indicates the green/red colour axis and b* the blue/yellow colour axis. The lower the value of L*, the darker or more intense the colour.

In particular, the coloration intensity DE* and the selectivity ΔE were compared between the dyeing process according to the invention and an identical dyeing process that does not involve the use of composition (A1) based on metal salts.

a. Calculation of the Colour Intensity (DE*)

In the table below, the value of DE* is calculated from the values of L*a*b* according to equation (i) below:

$$DE^* = \sqrt{(L^*-L_o^*)^2+(a^*-a_o^*)^2+(b^*-b_o^*)^2} \quad (i)$$

The coloration intensity is measured from the values L*, a* and b* measured on locks of natural grey hair after coloration or, alternatively, on locks of permanent-waved hair after coloration and $L_o^*$, $a_o^*$ and $b_o^*$ represent the values measured on natural undyed locks of hair or, respectively, on permanent-waved undyed locks of hair.

The greater the value of DE*, the more intense the coloration.

b. Gain in Coloration Intensity

The gain in coloration intensity is measured on natural hair (Gain on NG) from equation (ii) below:

Gain on $NG=DE^*$(with pretreatment with salts)$-DE^*$ (without pretreatment with salts)     (ii)

Calculation of the Selectivity

The value of ΔE (selectivity) is also calculated from the values of L*a*b* measured according to equation (iii) below:

$$\Delta E = \sqrt{(L-L_o^*)^2+(a^*-a_o^*)^2+(b^*-b_o^*)^2} \quad (iii)$$

In equation (iii), L*, a* and b* represent the values measured on locks of dyed natural grey hair and $L_o^*$, $a_o^*$ and $b_o^*$ represent the values measured on locks of permanent-waved dyed hair.

The coloration selectivity ΔE corresponds to the variation in colour between the natural hair, which is representative of the nature of the hair at the root, and the permanent-waved hair, which is representative of the nature of the hair at the end. The lower the value of ΔE, the greater the homogeneity between the end and the root of the hair.

All the results are given in the tables below.

TABLE 1

Results of the coloration intensity (DE*) on natural grey hair

|  | L* | a* | b* | DE* |
|---|---|---|---|---|
| Lock of untreated natural hair (NG) | 58.6 | 0.1 | 11.86 | — |
| Lock of natural hair treated with dye composition I without pretreatment (comparative) | 26.24 | −0.22 | −4.3 | 36.17 |
| Lock of natural hair treated with composition (A1) and dye composition I (invention) | 16.67 | 0.33 | −1.02 | 43.86 |

TABLE 2

Results of the coloration buildup (DE*) on permanent-waved hair

| | L* | a* | b* | DE* |
|---|---|---|---|---|
| Lock of untreated permanent-waved hair (PWG) | 58.46 | 1 | 14.92 | — |
| Lock of permanent-waved hair treated with dye composition I (comparative) | 17.39 | 0.09 | −2.03 | 44.4 |
| Lock of natural hair treated with composition (A1) and dye composition I (invention) | 14.3 | 0.15 | −0.77 | 46.87 |

It is observed that the dyeing process according to the invention produces a satisfactory coloration intensity both on locks of natural hair and on locks of permanent-waved hair.

TABLE 3

Result on the selectivity ΔE

| | ΔE |
|---|---|
| Lock of hair treated with dye composition I (comparative) | 9.14 |
| Lock of hair treated with composition (A1) and dye composition I (invention) | 2.39 |

It is found that the dyeing process produces sparingly selective colorations.

EXAMPLE 2

I. Compositions Tested

1. Preparation of the Composition Based on Metal Salts

Composition (A2) based on metal salts is prepared (the amounts are expressed as weight percentages).

| Composition | A2 |
|---|---|
| Cerium chloride heptahydrate | $8.2 \times 10^{-2}$ |
| Demineralized water | q.s. for 100 |
| pH | 5.46 |

3. Preparation of a Dye Composition I

A dye composition 2 is prepared from compositions (B), (C) and (D) described in Example 1.

II. Procedure

The procedure is identical to that described in Example 1.

III. Results

The intensity is evaluated as described in Example 1.

TABLE 1

Results of the coloration intensity (DE*) on natural grey hair

| | L* | a* | b* | DE* |
|---|---|---|---|---|
| Lock of untreated natural hair (NG) | 58.6 | 0.1 | 11.86 | — |
| Lock of natural hair treated with dye composition I (comparative) | 26.24 | −0.22 | −4.3 | 36.17 |
| Lock of natural hair treated with composition (A2) and dye composition I (invention) | 18.3 | 0.24 | −2.09 | 42.65 |

TABLE 2

Results of the coloration intensity (DE*) on locks of permanent-waved hair

| | L* | a* | b* | DE* |
|---|---|---|---|---|
| Lock of untreated permanent-waved hair (PWG) | 58.46 | 1 | 14.92 | — |
| Lock of permanent-waved hair treated with dye composition 2 (comparative) | 17.39 | 0.09 | −2.03 | 44.4 |
| Lock of permanent-waved hair treated with composition (A2) and dye composition 2 (invention) | 18.45 | 0.06 | −1.74 | 43.35 |

It is observed that the dyeing process produces a satisfactory coloration intensity, which is better on natural hair and similar on permanent-waved hair.

TABLE 4

Result on the selectivity ΔE

| | ΔE |
|---|---|
| Lock of hair treated with dye composition I (comparative) | 9.14 |
| Lock of hair treated with composition (A1) and dye composition I (invention) | 0.42 |

It is found that the dyeing process produces sparingly selective colorations.

EXAMPLE 3

I. Compositions Tested

1. Preparation of the Composition Based on Metal Salts

The composition based on metal salts corresponds to composition (A1).

2. Preparation of a Dye Composition I'

A dye composition I' is prepared from compositions (C) and (D) described in Example 1 and from composition (B') described below:

| Composition | B' |
|---|---|
| Oxidation base | $20 \times 10^{-3}$ mol % |
| Oxidation coupler | $20 \times 10^{-3}$ mol % |
| Monoethanolamine | 13.66 |
| Sodium metabisulfite | 0.70 |
| L-Ascorbic acid | 0.25 |
| Diethylenetriaminepentaacetic acid pentasodium salt as a 40% aqueous solution | 1 |

-continued

| Composition | B' |
|---|---|
| Hydroxyethyl cellulose | 1.5 |
| Propylene glycol | 6.2 |
| Ethanol | 8.25 |
| Hexylene glycol | 3.00 |
| Dipropylene glycol | 3.00 |
| Demineralized water | q.s. for 100 |

II. Procedure

The procedure is identical to that described in Example 1.

III. Results

The intensity is evaluated as described in Example 1.
Tables 1 and 2—Results of the Coloration Intensity (DE*) on Natural Grey Hair

TABLE 1

| Base | Coupler | Reference support B' + D + C | | | | Support of the invention A1 then B' + D + C | | | |
|---|---|---|---|---|---|---|---|---|---|
| | | L | a | b | ΔELab | L | a | b | ΔELab |
| 4-(3-Amino pyrazolo[1,5-a]pyrid-2-yl)-1,1-dimethyl-piperazin-1-ium chloride hydrochloride | Thymol | 44.51 | −8.45 | 6.21 | 26.2 | 24.2 | −4.38 | −8.41 | 41 |
| 4-(3-Amino pyrazolo[1,5-a]pyrid-2-yl)-1,1-dimethylpiperazin-1-ium chloride hydrochloride | Arbutin | 47.65 | −8.85 | 2.8 | 18.18 | 29.9 | 11.44 | −7 | 37.3 |

In both cases, better coloration intensity is observed with the process according to the invention.

EXAMPLE 4

I. Compositions Tested

1. Preparation of the Composition Based on Metal Salts

The composition based on metal salts corresponds to composition (A1).

2. Preparation of a Dye Composition 4

A dye composition I" is prepared from compositions (C) and (D) described in Example 1 and from composition (B") described below:

| Composition | B" |
|---|---|
| Oxidation coupler | $40 \times 10^{-3}$ mol % |
| Monoethanolamine | 13.66 |

TABLE 2

| Base | Coupler | Reference support B' + D + C | | | | Support of the invention A1 then B' + D + C | | | |
|---|---|---|---|---|---|---|---|---|---|
| | | L | a | b | ΔELab | L | a | b | ΔELab |
| 2-[(3-Amino-pyrazolo-[1,5-a]pyrid-2-yl)oxy]ethanol-hydrochloride hydrate | Thymol | 31.47 | 16.03 | 6.91 | 31.44 | 23.9 | 8.31 | 0.65 | 37.46 |
| 2-[(3-Amino-pyrazolo-[1,5a]pyrid-2-yl)oxy]ethanol-hydrochloride hydrate | Arbutin | 29.14 | 11.64 | −2.72 | 35.18 | 24.1 | 11.26 | −11.1 | 43.61 |

-continued

| Composition | B" |
|---|---|
| Sodium metabisulfite | 0.70 |
| L-Ascorbic acid | 0.25 |
| Diethylenetriaminepentaacetic acid pentasodium salt as a 40% aqueous solution | 1 |
| Hydroxyethyl cellulose | 1.5 |
| Propylene glycol | 6.2 |
| Ethanol | 8.25 |
| Hexylene glycol | 3.00 |
| Dipropylene glycol | 3.00 |
| Demineralized water | q.s. for 100 |

II. Procedure

The procedure is identical to that described in Example 1.

III. Results

The intensity is evaluated as described in Example 1.

TABLE 1

Results of the coloration intensity (DE*) on natural grey hair

| | Reference support B" + D + C | | | | Support of the invention A1 then B" + D + C | | | |
|---|---|---|---|---|---|---|---|---|
| Coupler | L | a | b | ΔELab* | L | a | b | ΔELab* |
| 1-β-hydroxy ethyloxy-2,4-diaminobenzene-dihydrochloride | 53.74 | 0.08 | 11.78 | 4.94 | 17.59 | 0.9 | 0.48 | 42.64 |
| 4-methoxy-1-naphthol | 63.13 | 0.25 | 13.18 | 5.36 | 27.47 | 2.95 | −18.46 | 44.8 |

In both cases, better coloration intensity is observed with the process according to the invention.

The invention claimed is:

1. A process for dyeing keratin fibres, comprising the use of one or more metal catalysts chosen from transition metal salts and rare-earth metal salts, and mixtures thereof, and of a composition (I) comprising:
   at least 10% of one or more fatty substances different from fatty acids relative to the total weight of composition (I),
   one or more oxidation dyes, and
   one or more oxidizing agents;
   wherein the one or more metal catalysts and the composition (I) provide a homogeneous coloration along the keratin fibres, when applied to the keratin fibres.

2. The process according to claim 1, characterized in that the metal salts are inorganic salts chosen from halides, carbonates, sulfates and phosphates.

3. The process according to claim 1, characterized in that the metal salts are organic acid salts chosen from citrates, lactates, glycolates, gluconates, acetates, propionates, fumarates, oxalates and tartrates.

4. The process according to claim 1, characterized in that the metal catalysts are chosen from organic acid salts of transition metals, and inorganic salts of rare-earth metals.

5. The process according to claim 1, characterized in that the fatty substances are chosen from $C_6$-$C_{16}$ hydrocarbons and hydrocarbons containing more than 16 carbon atoms and oils of plant origin, fatty alcohols, fatty acid and/or fatty alcohol esters, and silicones, or mixtures thereof.

6. The process according to claim 1, characterized in that the fatty substance(s) are chosen from oils that are liquid at room temperature and at atmospheric pressure.

7. The process according to claim 1, characterized in that the fatty substances are chosen from liquid petroleum jelly, polydecenes, liquid fatty alcohols and liquid esters of fatty acids or of fatty alcohols, or mixtures thereof.

8. The process according to claim 1, characterized in that the fatty substances are present in a content ranging from 10% to 70% by weight, relative to the total weight of composition (I).

9. The process according to claim 1, characterized in that the cosmetic composition (I) also comprises one or more surfactants.

10. The process according to claim 1, characterized in that the oxidation dyes are chosen from oxidation bases and/or couplers.

11. The process according to claim 10, characterized in that the oxidation bases are chosen from para-phenylenediamines, bis(phenyl)alkylenediamines, para-aminophenols, ortho-aminophenols, heterocyclic bases and the addition salts thereof, and the couplers are chosen from meta-phenylenediamines, meta-aminophenols, meta-diphenols, monophenols, naphthalene-based couplers and heterocyclic couplers, and also the addition salts thereof.

12. The process according to claim 1, characterized in that the oxidation dyes are chosen from mixtures of at least one heterocyclic oxidation base, and of at least one monophenolic coupler.

13. The process according to claim 1, characterized in that the oxidizing agent is hydrogen peroxide.

14. The process according to claim 1, characterized in that a composition (A) comprising the said metal catalyst(s) and composition (I) are mixed together, and the mixture made is then applied to wet or dry keratin fibres.

15. The process according to claim 1, characterized in that a composition (A) comprising the said metal catalyst(s) and composition (I) are successively applied to wet or dry keratin fibres, with or without intermediate rinsing.

16. The process according to claim 1, characterized in that composition (I) results from the mixing of two or three compositions including at least one composition (B) comprising one or more oxidation dyes and a composition (C) comprising one or more oxidizing agents and optionally a composition (D) comprising one or more fatty substances.

17. A multi-compartment device comprising a first compartment containing a cosmetic composition (A) comprising one or more metal catalysts chosen from transition metal salts and rare-earth metal salts, and mixtures thereof, a second compartment containing a cosmetic composition (B) comprising one or more oxidation dyes, and a third compartment containing a composition (C) comprising one or more oxidizing agents, at least one fatty substance different from fatty acids as defined in claim 1, the fatty substances being present in at least one of the compositions (B) or (C) such that, after mixing together the compositions (B) and (C), the fatty substance content is greater than or equal to 10% relative to the total weight of the mixture of compositions (B) and (C), and optionally a fourth compartment comprising a composition (D) comprising one or more fatty substances, the said composition (D) being intended to be mixed with compositions (B) and (C), the fatty substance content being greater than or equal to 10% relative to the total weight of the mixture of compositions (B), (C) and (D), composition (B) or (C) optionally containing one or more fatty substances.

18. The process according to claim 12, characterized in that the at least one monophenolic coupler is chosen from guaicol, arbutin, thymol, sesamol, carvacrol or syringol.

\* \* \* \* \*